United States Patent
Rankin et al.

(10) Patent No.: US 11,369,431 B2
(45) Date of Patent: Jun. 28, 2022

(54) INDUCTIVE DOUBLE FLAT COIL DISPLACEMENT SENSOR

(71) Applicant: Boston Scientific Scimed Inc., Maple Grove, MN (US)

(72) Inventors: Darrell L. Rankin, Milpitas, CA (US); John C. Potosky, San Jose, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 963 days.

(21) Appl. No.: 15/619,432

(22) Filed: Jun. 9, 2017

(65) Prior Publication Data

US 2017/0354467 A1    Dec. 14, 2017

Related U.S. Application Data

(60) Provisional application No. 62/348,905, filed on Jun. 11, 2016.

(51) Int. Cl.
*A61B 18/14* (2006.01)
*A61B 5/06* (2006.01)
(Continued)

(52) U.S. Cl.
CPC .......... *A61B 18/1492* (2013.01); *A61B 5/062* (2013.01); *A61B 5/065* (2013.01);
(Continued)

(58) Field of Classification Search
CPC . A61B 18/1492; A61B 5/6843; A61B 5/6852; A61B 90/06; A61B 5/062;
(Continued)

(56) References Cited

U.S. PATENT DOCUMENTS 4,930,494 A    6/1990    Takehana et al.
5,238,005 A    8/1993    Imran
(Continued)

FOREIGN PATENT DOCUMENTS

CN    101416874 A    4/2009
CN    102166136 A    8/2011
(Continued)

OTHER PUBLICATIONS

Hoffmayer, K.S., et al. "Contact Force-Sensing Catheters." Current Opinion in Cardiology, 30(1):74-80, Jan. 2015.
(Continued)

*Primary Examiner* — Amanda Lauritzen Moher
*Assistant Examiner* — Amy J Shafqat
(74) *Attorney, Agent, or Firm* — Faegre Drinker Biddle & Reath LLP

(57) ABSTRACT

A catheter adapted to measure a contact force includes a proximal segment, a distal segment, a spring segment extending from the proximal segment to the distal segment, and at least one inductive sensor. The at least one inductive sensor includes a first plate of high magnetic permeability material disposed on the proximal segment, a second plate of high magnetic permeability material disposed on the distal segment opposite the first plate, at least one first coil disposed adjacent to the first plate between the first plate and the second plate, and at least one second coil disposed adjacent to the second plate opposite the first coil between the first plate and the second plate. The second coil is electrically connected in series with the first coil. The first coil and the second coil are configured to output a signal indicative of displacement between the first coil and the second coil.

15 Claims, 6 Drawing Sheets

(51) Int. Cl.
  *A61M 25/01* (2006.01)
  *A61B 5/00* (2006.01)
  *A61B 90/00* (2016.01)
  *A61B 34/20* (2016.01)
  *A61B 18/00* (2006.01)
  *A61B 17/00* (2006.01)

(52) U.S. Cl.
  CPC .......... *A61B 5/6843* (2013.01); *A61B 5/6852* (2013.01); *A61B 90/06* (2016.02); *A61M 25/0127* (2013.01); *A61B 2017/00199* (2013.01); *A61B 2018/00351* (2013.01); *A61B 2018/00577* (2013.01); *A61B 2034/2051* (2016.02); *A61B 2090/065* (2016.02); *A61B 2090/3784* (2016.02); *A61M 2205/0216* (2013.01); *A61M 2205/0272* (2013.01)

(58) Field of Classification Search
  CPC ............ A61B 5/065; A61B 2090/3784; A61B 2034/2051; A61B 2090/065; A61B 2018/00577; A61B 2017/00199; A61B 2018/00351; A61M 25/0127; A61M 2205/0272; A61M 2205/0216; H01F 10/131–137; H01F 10/14–16; H01F 1/053–055; H01F 1/068; H01F 1/442–445; H01F 1/15316; H01F 1/15322; H01F 1/15325; H01F 10/3222; H01F 10/3236; H01F 10/3263–3268; H01F 10/3272; H01F 10/3281; H01F 10/1936; H01F 1/14708; H01F 1/344; H01F 1/348; H01F 27/361–366; H01F 41/046; H01F 7/02; H01F 21/08; G01R 33/383
  See application file for complete search history.

(56) References Cited

U.S. PATENT DOCUMENTS

| | | | |
|---|---|---|---|
| 5,293,869 A | 3/1994 | Edwards et al. | |
| 5,313,943 A | 5/1994 | Houser et al. | |
| 5,383,874 A | 1/1995 | Jackson et al. | |
| 5,471,982 A | 12/1995 | Edwards et al. | |
| 5,553,611 A | 9/1996 | Budd et al. | |
| 5,647,870 A | 7/1997 | Kordis et al. | |
| 5,836,990 A | 11/1998 | Li | |
| 5,904,680 A | 5/1999 | Kordis et al. | |
| 5,911,694 A | 6/1999 | Ikeda et al. | |
| 5,911,739 A | 6/1999 | Kordis et al. | |
| 5,968,040 A | 10/1999 | Swanson et al. | |
| 6,014,590 A | 1/2000 | Whayne et al. | |
| 6,152,899 A | 11/2000 | Farley et al. | |
| 6,165,169 A | 12/2000 | Panescu et al. | |
| 6,216,043 B1 | 4/2001 | Swanson et al. | |
| 6,371,928 B1 | 4/2002 | McFann et al. | |
| 6,690,963 B2 * | 2/2004 | Ben-Haim | A61N 1/36564 600/117 |
| 6,695,808 B2 | 2/2004 | Tom | |
| 6,864,418 B2 * | 3/2005 | Wang | A61N 1/16 174/391 |
| 7,637,903 B2 | 12/2009 | Lentz et al. | |
| 7,658,715 B2 | 2/2010 | Park et al. | |
| 7,720,420 B2 | 5/2010 | Kajita | |
| 8,357,152 B2 | 1/2013 | Govari et al. | |
| 8,374,670 B2 | 2/2013 | Selkee | |
| 8,496,653 B2 | 7/2013 | Steinke | |
| 8,529,476 B2 | 9/2013 | Govari | |
| 8,684,010 B2 * | 4/2014 | Shachar | A61B 1/041 128/899 |
| 8,911,382 B2 | 12/2014 | Hauck et al. | |
| 9,060,782 B2 | 6/2015 | Daniel et al. | |
| 9,125,565 B2 | 9/2015 | Hauck | |
| 9,486,272 B2 | 11/2016 | Bonyak et al. | |
| 9,510,786 B2 | 12/2016 | Gliner | |
| 9,974,608 B2 | 5/2018 | Gliner et al. | |
| 10,022,190 B2 | 7/2018 | Valsamis et al. | |
| 10,595,745 B2 * | 3/2020 | Byron | A61B 18/1492 |
| 2001/0047133 A1 * | 11/2001 | Gilboa | A61B 34/20 600/429 |
| 2003/0056599 A1 | 3/2003 | Van et al. | |
| 2003/0069522 A1 | 4/2003 | Jacobsen et al. | |
| 2003/0130615 A1 * | 7/2003 | Tom | A61B 5/6852 604/65 |
| 2004/0176699 A1 | 9/2004 | Walker et al. | |
| 2005/0096647 A1 | 5/2005 | Steinke et al. | |
| 2006/0189896 A1 | 8/2006 | Davis et al. | |
| 2006/0235286 A1 | 10/2006 | Stone et al. | |
| 2007/0016063 A1 | 1/2007 | Park et al. | |
| 2007/0156209 A1 | 7/2007 | Laufer et al. | |
| 2007/0191829 A1 | 8/2007 | McGee et al. | |
| 2008/0015568 A1 | 1/2008 | Paul et al. | |
| 2008/0051704 A1 | 2/2008 | Patel et al. | |
| 2008/0161796 A1 * | 7/2008 | Cao | A61B 18/1492 606/41 |
| 2008/0262489 A1 | 10/2008 | Steinke | |
| 2008/0319350 A1 | 12/2008 | Wallace et al. | |
| 2008/0319436 A1 | 12/2008 | Daniel et al. | |
| 2009/0076476 A1 | 3/2009 | Barbagli et al. | |
| 2009/0076498 A1 | 3/2009 | Saadat et al. | |
| 2009/0093806 A1 | 4/2009 | Govari et al. | |
| 2009/0099551 A1 | 4/2009 | Tung et al. | |
| 2009/0306650 A1 | 12/2009 | Govari et al. | |
| 2010/0063492 A1 | 3/2010 | Kahlert et al. | |
| 2010/0168557 A1 | 7/2010 | Deno et al. | |
| 2010/0168620 A1 | 7/2010 | Klimovitch et al. | |
| 2010/0305429 A1 * | 12/2010 | Shachar | A61B 5/1075 600/424 |
| 2011/0058862 A1 * | 3/2011 | Yamaguchi | G03G 15/2039 399/329 |
| 2011/0130648 A1 * | 6/2011 | Beeckler | A61B 18/1492 600/424 |
| 2011/0144509 A1 | 6/2011 | Kahlert et al. | |
| 2011/0160556 A1 * | 6/2011 | Govari | A61B 5/6852 600/374 |
| 2011/0184406 A1 * | 7/2011 | Selkee | A61B 5/6885 606/41 |
| 2011/0218491 A1 | 9/2011 | Hauck et al. | |
| 2012/0035495 A1 | 2/2012 | Gutfinger et al. | |
| 2012/0041295 A1 | 2/2012 | Schultz | |
| 2012/0259238 A1 | 10/2012 | Gunday et al. | |
| 2012/0265102 A1 | 10/2012 | Leo et al. | |
| 2012/0271135 A1 | 10/2012 | Burke et al. | |
| 2012/0283713 A1 | 11/2012 | Mihalik et al. | |
| 2012/0283714 A1 | 11/2012 | Mihalik et al. | |
| 2012/0283715 A1 | 11/2012 | Mihalik et al. | |
| 2012/0330190 A1 | 12/2012 | Gliner | |
| 2013/0066220 A1 | 3/2013 | Weinkam et al. | |
| 2013/0172715 A1 | 7/2013 | Just et al. | |
| 2013/0289369 A1 | 10/2013 | Margolis | |
| 2013/0310702 A1 | 11/2013 | Reinders et al. | |
| 2014/0025069 A1 | 1/2014 | Willard et al. | |
| 2014/0031785 A1 | 1/2014 | Schwagten et al. | |
| 2014/0081264 A1 | 3/2014 | Fandrey et al. | |
| 2014/0113828 A1 * | 4/2014 | Gilbert | H01B 1/00 505/100 |
| 2014/0121660 A1 | 5/2014 | Hauck | |
| 2014/0128949 A1 | 5/2014 | Hollett et al. | |
| 2014/0225700 A1 * | 8/2014 | Doyle | H01L 25/105 336/200 |
| 2014/0276006 A1 * | 9/2014 | Sliwa | A61B 8/0841 600/424 |
| 2014/0276078 A1 | 9/2014 | Schweitzer et al. | |
| 2014/0276760 A1 | 9/2014 | Bonyak et al. | |
| 2014/0276787 A1 | 9/2014 | Wang et al. | |
| 2014/0364848 A1 * | 12/2014 | Heimbecher | A61B 5/6885 606/41 |
| 2015/0066021 A1 | 3/2015 | Gliner et al. | |
| 2015/0157400 A1 | 6/2015 | Gelbart et al. | |
| 2015/0190616 A1 | 7/2015 | Salvestro et al. | |
| 2015/0223757 A1 | 8/2015 | Werneth et al. | |

(56) References Cited

U.S. PATENT DOCUMENTS

| | | |
|---|---|---|
| 2015/0300895 A1 | 10/2015 | Matsudate et al. |
| 2015/0351652 A1 | 12/2015 | Marecki et al. |
| 2015/0351836 A1 | 12/2015 | Prutchi |
| 2015/0369373 A1 | 12/2015 | Reith et al. |
| 2016/0022373 A1 | 1/2016 | Valsamis et al. |
| 2016/0113582 A1 | 4/2016 | Altmann et al. |
| 2016/0187208 A1* | 6/2016 | Michael ............ B23Q 3/15 73/862.53 |
| 2016/0228180 A1* | 8/2016 | Sliwa ............... A61B 5/6885 |
| 2016/0276739 A1* | 9/2016 | Buesseler ............ H01Q 7/06 |
| 2016/0278852 A1 | 9/2016 | Sliwa et al. |
| 2016/0296333 A1 | 10/2016 | Balachandran et al. |
| 2016/0351292 A1 | 12/2016 | Toth et al. |
| 2017/0035358 A1 | 2/2017 | Rankin |
| 2017/0035991 A1 | 2/2017 | Rankin et al. |
| 2017/0143416 A1* | 5/2017 | Guler ............... A61B 5/6852 |
| 2017/0165000 A1 | 6/2017 | Basu et al. |
| 2017/0172509 A1 | 6/2017 | Hein et al. |
| 2017/0199064 A1 | 7/2017 | Lozano |
| 2017/0215802 A1 | 8/2017 | Byron et al. |
| 2017/0238991 A1* | 8/2017 | Worrell ............. H05K 3/061 |
| 2017/0290617 A1 | 10/2017 | Rankin et al. |
| 2017/0296084 A1 | 10/2017 | Blauer et al. |
| 2018/0078218 A1 | 3/2018 | Moisa et al. |
| 2018/0264225 A1 | 9/2018 | Sardari et al. |
| 2018/0360533 A1 | 12/2018 | Olson |
| 2019/0059818 A1 | 2/2019 | Herrera et al. |

FOREIGN PATENT DOCUMENTS

| | | |
|---|---|---|
| CN | 102652690 A | 9/2012 |
| CN | 103607961 A | 2/2014 |
| DE | 102009037044 A1 | 3/2011 |
| EP | 1169974 A1 | 1/2002 |
| EP | 1803410 A1 | 7/2007 |
| EP | 2047797 A2 | 4/2009 |
| EP | 2172240 A1 | 4/2010 |
| EP | 2526887 A1 | 11/2012 |
| EP | 2662015 B1 | 11/2013 |
| EP | 2732760 A1 | 5/2014 |
| EP | 2862537 A1 | 4/2015 |
| WO | 1995010978 A1 | 4/1995 |
| WO | 2001070117 A2 | 9/2001 |
| WO | 2002021995 A2 | 3/2002 |
| WO | 2015069887 A1 | 5/2015 |

OTHER PUBLICATIONS

International Search Report and the Written Opinion issued in PCT/US2016/045303, dated Oct. 20, 2016, 15 pages.
International Search Report and Written Opinion issued in PCT/US2016/045907, dated Oct. 20, 2016, 10 pages.
International Search Report and Written Opinion issued in PCT/US2016/062976, dated Feb. 8, 2017, 12 pages.
International Search Report and Written Opinion issued in PCT/US2016/067629, dated Mar. 17, 2017, 13 pages.
International Search Report and Written Opinion issued in PCT/US2017015426, dated May 10, 2017, 13 pages.
Internatilonal Preliminary Report on Patentability issued in PCT/US2016/045303, dated Feb. 22, 2018, 9 pages.
International Preliminary Report on Patentability issued in PCT/US2016/045907, dated Feb. 22, 2018, 7 pages.
International Preliminary Report on Patentability issued in PCT/US2016/062976, dated May 31, 2018, 8 pages.
Rafael, A. and Heist, E. K. (2015). Innovative Techniques: Techniques to Optimize Catheter Contact Force during Ablation of Atrial Fibrillation. The Journal of Innovations in Cardiac Rhythm Management, 6:1990-1995.

* cited by examiner

INDUCTIVE DOUBLE FLAT COIL DISPLACEMENT SENSOR

CROSS-REFERENCE TO RELATED APPLICATION

This application claims priority to Provisional Application No. 62/348,905, filed Jun. 11, 2016, which is herein incorporated by reference in its entirety.

TECHNICAL FIELD

The present disclosure relates generally to various force sensing catheter features.

BACKGROUND

In ablation therapy, it may be useful to assess the contact between the ablation element and the tissue targeted for ablation. In interventional cardiac electrophysiology (EP) procedures, for example, the contact can be used to assess the effectiveness of the ablation therapy being delivered. Other catheter-based therapies and diagnostics can be aided by knowing whether a part of the catheter contacts targeted tissue, and to what degree the part of the catheter presses on the targeted tissue. The tissue exerts a force back on the catheter, which can be measured to assess the contact and the degree to which the catheter presses on the targeted tissue.

The present disclosure concerns, amongst other things, systems for measuring a force with a catheter.

SUMMARY

Example 1 is a catheter adapted to measure a contact force. The catheter includes a proximal segment, a distal segment, a spring segment extending from the proximal segment to the distal segment, and at least one inductive sensor. The spring segment is configured to permit displacement between the distal segment and the proximal segment in response to an application of the force on the distal segment. The at least one inductive sensor includes a first plate of high magnetic permeability material disposed on the proximal segment, a second plate of high magnetic permeability material disposed on the distal segment opposite the first plate, at least one first coil disposed adjacent to the first plate between the first plate and the second plate, and at least one second coil disposed adjacent to the second plate opposite the first coil between the first plate and the second plate. The second coil is electrically connected in series with the first coil. The first coil and the second coil are configured to output a signal indicative of the displacement between the first coil and the second coil.

In Example 2, the catheter of Example 1, wherein edges of the first plate of high magnetic permeability material extend beyond edges of the at least one first coil and edges of the second plate of high magnetic permeability material extend beyond edges of the at least one second coil.

In Example 3, the catheter of either of Examples 1 or 2, wherein the at least one first coil includes a plurality of axially spaced coils electrically connected in series and the at least one second coil includes a plurality of axially spaced coils electrically connected in series.

In Example 4, the catheter of any of Examples 1-3, wherein the at least one first coil is a flat coil of one or more flexible printed circuit conductive layers and the at least one second coil is a flat coil of one or more flexible printed circuit conductive layers.

In Example 5, the catheter of any of Examples 1-4, wherein the at least one inductive sensor includes a plurality of inductive sensors.

In Example 6, the catheter of Example 5, wherein the plurality of inductive sensors are circumferentially arrayed evenly about a longitudinal axis.

In Example 7, the catheter of Example either of Examples 5 or 6, wherein the plurality of inductive sensor consists of three inductive sensors.

In Example 8, the catheter of any of Examples 1-7, wherein the distal segment includes an ablation element configured to deliver ablation therapy.

In Example 9, the catheter of any of Examples 1-8, wherein the first plate of high magnetic permeability material and the second plate of high magnetic permeability material each have a relative permeability greater than 1000.

In Example 10, the catheter of any of Examples 1-9, wherein the signal indicative of the displacement between the at least one first coil and the at least one second coil is a change in an alternating voltage amplitude resulting at least in part from changes in a degree of magnetic flux interaction between the first coil and the second coil caused by changes in a distance between the first coil and the second coil.

Example 11 is a system adapted to measure a catheter contact force. The system includes a catheter according to any of Examples 5-10 and control circuitry configured to receive, for each of the plurality of inductive sensors, the signal indicative of the displacement between the at least one first coil and the at least one second coil, and calculate at least one of a magnitude and a direction of the contact force based at least in part on the received signals.

In Example 12, the system of Example 11, wherein the spring segment includes an elastic element connecting the proximal segment to the distal segment to permit displacement between the distal segment and the proximal segment in response to an application of the force on the distal segment, wherein the control circuitry is further configured to calculate the at least one of the magnitude and the direction of the contact force based at least in part on a spring constant for the elastic element.

In Example 13, the system of either of Examples 11 or 12, wherein the control circuitry is further configured to deliver an alternating sinusoidal electrical current to the at least one first coil and the at least one second coil of each of the plurality of inductive sensors to produce an alternating voltage across the first coil and the second coil.

In Example 14, the system of any of Example 11-13, further comprising a display, wherein the at least one parameter comprises a magnitude and a direction of the force and the control circuitry is configured to graphically indicate on the display the magnitude and the direction of the force.

Example 15 is a method of determining a contact force exerted on a distal segment of a catheter having an elastic element disposed between a proximal segment and the distal segment, and a plurality of inductive sensors each having at least one first coil adjacent to a first plate of high magnetic permeability material disposed on the proximal segment and at least one second coil connected in series to the first coil, the second coil adjacent to a second plate of high magnetic permeability material disposed on the distal segment. The method includes delivering an alternating sinusoidal electrical current to the first coil and the second coil of each of the inductive sensors to produce an alternating voltage across the first coil and the second coil; measuring an amplitude of the alternating voltage produced across the first coil and the second coil for each of the inductive sensors, wherein for at least one of the inductive sensors, the amplitude of the alternating voltage produced across the first coil and the second coil increases as the contact force is exerted on the distal segment of the catheter by displacing the first coil toward the second coil, increasing both a degree of magnetic flux interaction between the first coil and the second coil and an effective magnetic permeability for the first coil and the second coil; and calculating at least one of the magnitude and the direction of the contact force based on the measured amplitude of the alternating voltage produced across the first coil and the second coil for each of the inductive sensors and on a spring constant for the elastic element.

Example 16 is a catheter adapted to measure a contact force. The catheter includes a proximal segment, a distal segment, a spring segment extending from the proximal segment to the distal segment, and a plurality of inductive sensors. The spring segment is configured to permit displacement between the distal segment and the proximal segment in response to an application of the force on the distal segment. Each inductive sensor includes a first plate of high magnetic permeability material disposed on the proximal segment, a second plate of high magnetic permeability material disposed on the distal segment opposite the first plate, at least one first coil disposed adjacent to the first plate between the first plate and the second plate, and at least one second coil disposed adjacent to the second plate opposite the first coil between the first plate and the second plate. The second coil is electrically connected in series with the first coil. The first coil and the second coil are configured to output a signal indicative of the displacement between the first coil and the second coil.

In Example 17, The catheter of Example 16, wherein edges of the first plate of high magnetic permeability material extend beyond edges of the at least one first coil and edges of the second plate of high magnetic permeability material extend beyond edges of the at least one second coil.

In Example 18, the catheter of either of Examples 16 or 17, wherein the at least one first coil includes a plurality of axially spaced coils electrically connected in series and the at least one second coil includes a plurality of axially spaced coils electrically connected in series.

In Example 19, the catheter of any of Examples 16-18, wherein the at least one first coil is a flat coil of one or more flexible printed circuit conductive layers and the at least one second coil is a flat coil of one or more flexible printed circuit conductive layers.

In Example 20, the catheter of any of Examples 16-19, wherein the plurality of inductive sensors consists of three inductive sensors circumferentially arrayed evenly about a longitudinal axis.

In Example 21, the catheter of any of Examples 16-20, wherein the distal segment includes an ablation element configured to deliver ablation therapy.

In Example 22, the catheter of any of Examples 16-21, wherein the first plate of high magnetic permeability material and the second plate of high magnetic permeability material each have a relative permeability greater than 1000.

In Example 23, the catheter of any of Examples 16-22, wherein the spring segment includes an elastic element connecting the proximal segment to the distal segment to permit displacement between the distal segment and the proximal segment in response to an application of the force on the distal segment and to resiliently reverse the displacement upon removal of the force from the distal segment.

In Example 24, the catheter of any of Examples 16-23, wherein the signal indicative of the displacement between the at least one first coil and the at least one second coil is a change in an alternating voltage amplitude resulting a least in part from changes in a degree of magnetic flux interaction between the first coil and the second coil caused by changes in a distance between the first coil and the second coil.

Example 25 is a system adapted to measure a catheter contact force. The system includes a catheter and control circuitry. The catheter includes a proximal segment, a distal segment, a spring segment extending from the proximal segment to the distal segment, and a plurality of inductive sensors. The spring segment is configured to permit displacement between the distal segment and the proximal segment in response to an application of the force on the distal segment. Each inductive sensor includes a first plate of high magnetic permeability material disposed on the proximal segment, a second plate of high magnetic permeability material disposed on the distal segment opposite the first plate, at least one first coil disposed adjacent to the first plate between the first plate and the second plate, and at least one second coil disposed adjacent to the second plate between the first plate and the second plate opposite the first coil. The second coil electrically connected in series with the first coil. The first coil and the second coil are configured to output a signal indicative of the displacement between the first coil and the second coil. The control circuitry is configured to receive, for each of the plurality of inductive sensors, the signal indicative of the displacement between the at least one first coil and the at least one second coil, and calculate at least one of a magnitude and a direction of the contact force based at least in part on the received signals.

In Example 26, the system of Example 25, wherein the spring segment includes an elastic element connecting the proximal segment to the distal segment to permit displacement between the distal segment and the proximal segment in response to an application of the force on the distal segment, wherein the control circuitry is further configured to calculate the at least one of the magnitude and the direction of the contact force based at least in part on a spring constant for the elastic element.

In Example 27, the system of either of Examples 25 or 26, wherein the control circuitry is further configured to deliver an alternating sinusoidal electrical current to the at least one first coil and the at least one second coil of each of the plurality of inductive sensors to produce an alternating voltage across the first coil and the second coil.

In Example 28, the system of any of Examples 25-27, further comprising a display, wherein the at least one parameter comprises a magnitude and a direction of the force and the control circuitry is configured to graphically indicate on the display the magnitude and the direction of the force.

In Example 29, the system of any of Examples 25-28, wherein edges of the first plate of high magnetic permeability material extend beyond edges of the at least one first coil and edges of the second plate of high magnetic permeability material extend beyond edges of the at least one second coil.

In Example 30, the system of any of Examples 25-29, wherein the at least one first coil includes a plurality of axially spaced coils electrically connected in series and the at least one second coil includes a plurality of axially spaced coils electrically connected in series.

In Example 31, the system of any of Examples 25-30, wherein the at least one first coil is a flat coil of one or more flexible printed circuit conductive layers and the at least one second coil is a flat coil of one or more flexible printed circuit conductive layers.

In Example 32, the system of any of Examples 25-31, wherein the plurality of inductive sensors consists of three inductive sensors circumferentially arrayed evenly about a longitudinal axis.

In Example 33, the system of any of Examples 25-32, wherein the distal segment includes an ablation element configured to deliver ablation therapy.

In Example 34, the system of any of Examples 25-33, wherein the signal indicative of the displacement between the at least one first coil and the at least one second coil is a change in an alternating voltage amplitude resulting from changes in a degree of magnetic flux interaction between the first coil and the second coil caused by changes in a distance between the first coil and the second coil.

Example 35 is a method of determining a contact force exerted on a distal segment of a catheter having an elastic element disposed between a proximal segment and the distal segment, and a plurality of inductive sensors each having at least one first coil adjacent to a first plate of high magnetic permeability material disposed on the proximal segment and at least one second coil connected in series to the first coil, the second coil adjacent to a second plate of high magnetic permeability material disposed on the distal segment. The method includes delivering an alternating sinusoidal electrical current to the first coil and the second coil of each of the inductive sensors to produce an alternating voltage across the first coil and the second coil; measuring an amplitude of the alternating voltage produced across the first coil and the second coil for each of the inductive sensors, wherein for at least one of the inductive sensors, the amplitude of the alternating voltage produced across the first coil and the second coil increases as the contact force is exerted on the distal segment of the catheter by displacing the first coil toward the second coil, increasing both a degree of magnetic flux interaction between the first coil and the second coil and an effective magnetic permeability for the first coil and the second coil; and calculating at least one of the magnitude and the direction of the contact force based on the measured amplitude of the alternating voltage produced across the first coil and the second coil for each of the inductive sensors and on a spring constant for the elastic element.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1A:
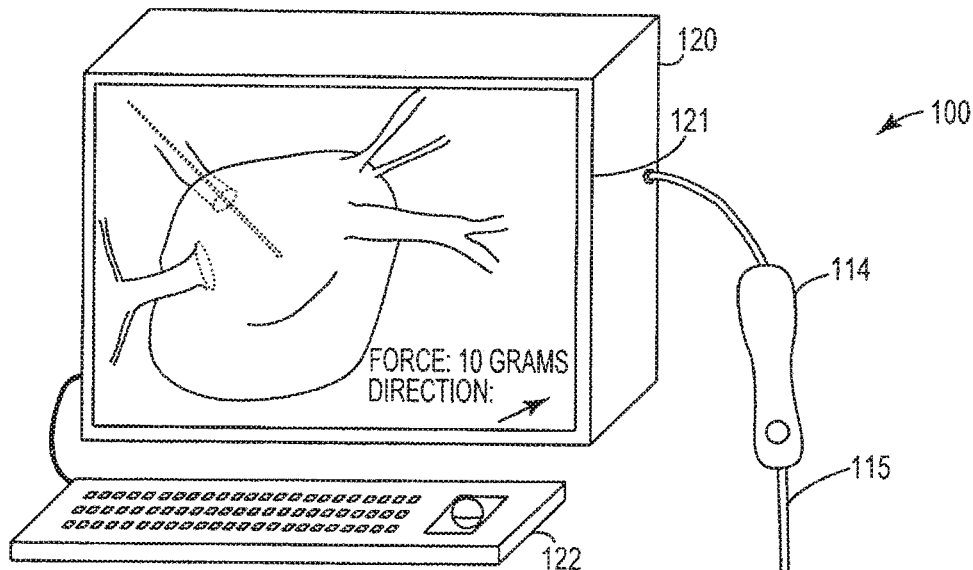
FIGS. 1A-1C show a system for measuring a force with a catheter in accordance with various embodiments of this disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various cardiac abnormalities can be attributed to improper electrical activity of cardiac tissue. Such improper electrical activity can include, but is not limited to, generation of electrical signals, conduction of electrical signals, and/or mechanical contraction of the tissue in a manner that does not support efficient and/or effective cardiac function. For example, an area of cardiac tissue may become electrically active prematurely or otherwise out of synchrony during the cardiac cycle, thereby causing the cardiac cells of the area and/or adjacent areas to contract out of rhythm. The result is an abnormal cardiac contraction that is not timed for optimal cardiac output. In some cases, an area of cardiac tissue may provide a faulty electrical pathway (e.g., a short circuit) that causes an arrhythmia, such as atrial fibrillation or supraventricular tachycardia. In some cases, inactivate tissue (e.g., scar tissue) may be preferable to malfunctioning cardiac tissue.

Cardiac ablation is a procedure by which cardiac tissue is treated to inactivate the tissue. The tissue targeted for ablation may be associated with improper electrical activity, as described above. Cardiac ablation can lesion the tissue and prevent the tissue from improperly generating or conducting electrical signals. For example, a line, a circle, or other formation of lesioned cardiac tissue can block the propagation of errant electrical signals. In some cases, cardiac ablation is intended to cause the death of cardiac tissue and to have scar tissue reform over the lesion, where the scar tissue is not associated with the improper electrical activity. Lesioning therapies include electrical ablation, radiofrequency ablation, cyroablation, microwave ablation, laser ablation, and surgical ablation, among others. While cardiac ablation therapy is referenced herein as an exemplar, various embodiments of the present disclosure can be directed to ablation of other types of tissue and/or to non-ablation diagnostic and/or catheters that deliver other therapies.

Ideally, an ablation therapy can be delivered in a minimally invasive manner, such as with a catheter introduced into the heart through a vessel, rather than surgically opening the heart for direct access (e.g., as in a maze surgical procedure). For example, a single catheter can be used to perform an electrophysiology study of the inner surfaces of a heart to identify electrical activation patterns. From these patterns, a clinician can identify areas of inappropriate electrical activity and ablate cardiac tissue in a manner to kill or isolate the tissue associated with the inappropriate electrical activation. However, the lack of direct access in a catheter-based procedure may require that the clinician only interact with the cardiac tissue through a single catheter and keep track of all of the information that the catheter collects or is otherwise associated with the procedure. In particular, it can be challenging to determine the location of the therapy element (e.g., the proximity to tissue), the quality of a lesion, and whether the tissue is fully lesioned, under-lesioned (e.g., still capable of generating and/or conducting unwanted electrical signals), or over-lesioned (e.g., burning through or otherwise weakening the cardiac wall). The quality of the lesion can depend on the degree of contact between the ablation element and the targeted tissue. For example, an ablation element that is barely contacting tissue may not be adequately positioned to deliver effective ablation therapy. Conversely, an ablation element that is pressed too hard into tissue may deliver too much ablation energy or cause a perforation.

The present disclosure concerns, among other things, methods, devices, and systems for assessing a degree of contact between a part of a catheter (e.g., an ablation element) and tissue. Knowing the degree of contact, such as the magnitude and the direction of a force generated by contact between the catheter and the tissue, can be useful in determining the degree of lesioning of the targeted tissue. Information regarding the degree of lesioning of cardiac tissue can be used to determine whether the tissue should be further lesioned or whether the tissue was successfully ablated, among other things. Additionally or alternatively, an indicator of contact can be useful when navigating the catheter because a user may not feel a force being exerted on the catheter from tissue as the catheter is advanced within a patient, thereby causing vascular or cardiac tissue damage or perforation.

Figure 1B:
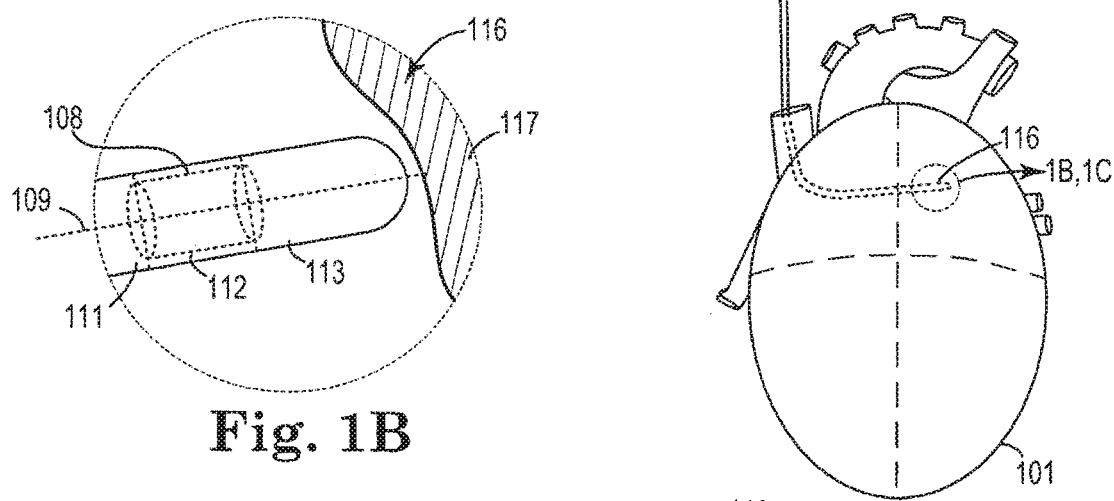
Figure 1C:
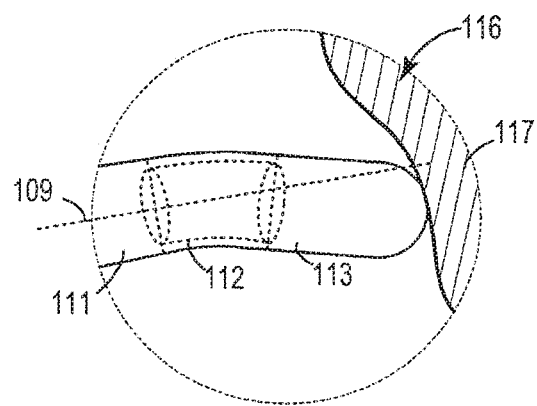

FIGS. 1A-1C illustrate an embodiment of a system 100 for sensing data from inside the body and/or delivering therapy. For example, the system 100 can be configured to map cardiac tissue and/or ablate the cardiac tissue, among other options. The system 100 includes a catheter 110 connected to a control unit 120 via handle 114. The catheter 110 can comprise an elongated tubular member having a proximal end 115 connected with the handle 114 and a distal end 116 configured to be introduced within a heart 101 or other area of the body. As shown in FIG. 1A, the distal end 116 of the catheter 110 is within the left atrium of the heart 101.

As shown in FIG. 1B, the distal end 116 of the catheter 110 includes a proximal segment 111, a spring segment 112, and a distal segment 113. The proximal segment 111, the spring segment 112, and the distal segment 113 can be coaxially aligned with each other in a base orientation as shown in FIG. 1B. Specifically, in the illustrated embodiment, each of the proximal segment 111, the spring segment 112, and the distal segment 113 are coaxially aligned with a common longitudinal axis 109. In one embodiment, the longitudinal axis 109 can extend through the radial center of each of the proximal segment 111, the spring segment 112, and the distal segment 113, and can extend through the radial center of the distal end 116 as a whole. In some embodiments, the coaxial alignment of the proximal segment 111 with the distal segment 113 can correspond to the base orientation. As shown, the distal end 116, at least along the proximal segment 111, the spring segment 112, and the distal segment 113, extends straight. In some embodiments, this straight arrangement of the proximal segment 111, the spring segment 112, and the distal segment 113 can correspond to the base orientation.

The distal segment 113, or any other segment, can be in the form of an electrode configured for sensing electrical activity, such as electrical cardiac signals. In other embodiments, such an electrode can additionally or alternatively be used to deliver ablative energy to tissue.

The catheter 110 includes force sensing capabilities. For example, as shown in FIGS. 1B and 1C, the catheter 110 is configured to sense a force exerted upon the distal segment 113 due to engagement of the distal segment 113 with tissue 117 of heart 101. In various embodiments, the distal segment 113 can be relatively rigid while segments proximal of the distal segment 113 can be relatively flexible. In particular, the spring segment 112 may be more flexible than the distal segment 113 and the proximal segment 111 such that when the distal end 116 of the catheter 110 engages the tissue 117, the spring segment 112 bends, as shown in FIG. 1C. For example, the distal end 116 of the catheter 110 can be generally straight as shown in FIG. 1B. When the distal segment 113 engages tissue 117, the distal segment 113 of the catheter 110 can be deflected relative to the proximal segment 111 as a result of bending and/or compression of the spring segment 112. As shown in FIGS. 1B and 1C, the applied force from the tissue moves the distal segment 113 out of coaxial alignment (e.g., with respect to the longitudinal axis 109) with the proximal segment 111 while the spring segment 112 bends. As such, proximal segment 111 and the distal segment 113 may be stiff to not bend due to the force while the spring segment 112 may be less stiff and bend to accommodate the force exerted on the distal segment 113. One or more sensors within the distal end 116 of the catheter 110 can sense the degree of bending or axial compression of the spring segment 112 to determine the magnitude and the direction of the force, as further discussed herein. When the distal segment 113 no longer engages the tissue 117, the spring segment 112 may return the proximal segment 111, the spring segment 112, and the distal segment 113 to the base orientation shown in FIG. 1B.

The control unit 120 of the system 100 includes a display 121 (e.g., a liquid crystal display or a cathode ray tube) for displaying information. The control unit 120 further includes a user input 122 which can include one or more buttons, toggles, a track ball, a mouse, touchpad, or the like for receiving user input. The user input 122 can additionally or alternatively be located on the handle 114. The control unit 120 can contain control circuitry for performing the functions referenced herein. Some or all of the control circuitry can alternatively be located within the handle 114.

Figure 2:
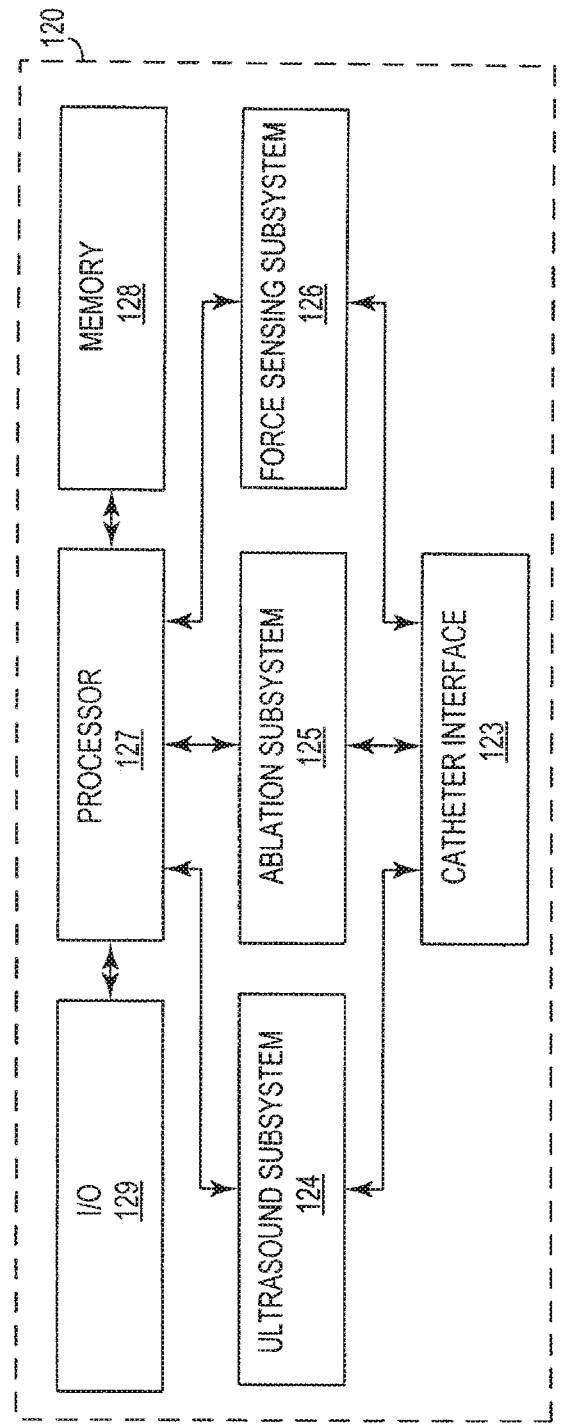
FIG. 2 shows a block diagram of circuitry for controlling various functions described herein.

FIG. 2 illustrates a block diagram showing an example of control circuitry which can perform functions referenced herein. This or other control circuitry can be housed within control unit 120, which can comprise a single housing or multiple housings among which components are distributed. Control circuitry can additionally or alternatively be housed within the handle 114. The components of the control unit 120 can be powered by a power supply (not shown), as known in the art, which can supply electrical power to any of the components of the control unit 120 and the system 100. The power supply can plug into an electrical outlet and/or provide power from a battery, among other options.

The control unit 120 can include a catheter interface 123. The catheter interface 123 can include a plug which receives a cord from the handle 114. The catheter 110 can include multiple conductors (not illustrated but known in the art) to convey electrical signals between the distal end 116 and the proximal end 115 and further to the catheter interface 123. It is through the catheter interface 123 that the control unit 120 (and/or the handle 114 if control circuitry is included in the handle 114) can send electrical signals to any element within the catheter 110 and/or receive an electrical signal from any element within the catheter 110. The catheter interface 123 can conduct signals to any of the components of the control unit 120.

The control unit 120 can include hardware and software for use in imaging the tissue being mapped and/or treated.

For example, in one embodiment, the control unit 120 can include an ultrasound subsystem 124 which includes components for operating the ultrasound functions of the system 100. While the illustrated example of control circuitry shown in FIG. 2 includes the ultrasound subsystem 124, it will be understood that not all embodiment may include ultrasound subsystem 124 or any circuitry for imaging tissue. The ultrasound subsystem 124 can include a signal generator configured to generate a signal for ultrasound transmission and signal processing components (e.g., a high pass filter) configured to filter and process reflected ultrasound signals as received by an ultrasound transducer in a sense mode and conducted to the ultrasound subsystem 124 through a conductor in the catheter 110. The ultrasound subsystem 124 can send signals to elements within the catheter 110 via the catheter interface 123 and/or receive signals from elements within the catheter 110 via the catheter interface 123.

It is emphasized, however, that the ultrasound subsystem 124, or other types of imaging subsystems, are strictly optional, and need not be included in the control unit 120.

The control unit 120 can include an ablation subsystem 125. The ablation subsystem 125 can include components for operating the ablation functions of the system 100. While the illustrated example of control circuitry shown in FIG. 2 includes the ablation subsystem, it will be understood that not all embodiment may include ablation subsystem 125 or any circuitry for generating an ablation therapy. The ablation subsystem 125 can include an ablation generator to provide different therapeutic outputs depending on the particular configuration (e.g., a high frequency alternating current signal in the case of radiofrequency ablation to be output through one or more electrodes). Providing ablation energy to target sites is further described, for example, in U.S. Pat. Nos. 5,383,874 and 7,720,420, each of which is expressly incorporated herein by reference in its entirety for all purposes. The ablation subsystem 125 may support any other type of ablation therapy, such as microwave ablation. The ablation subsystem 125 can deliver signals or other type of ablation energy through the catheter interface 123 to the catheter 110.

The control unit 120 can include a force sensing subsystem 126. The force sensing subsystem 126 can include components for measuring a force experienced by the catheter 110. Such components can include signal processors, analog-to-digital converters, operational amplifiers, comparators, and/or any other circuitry for conditioning and measuring one or more signals. The force sensing subsystem 126 can send electrical current to sensors, such as inductive sensors 144 (discussed below in reference to FIGS. 4-6), within the catheter 110 via the catheter interface 123 and receive signals from sensors within the catheter 110 via the catheter interface 123.

Each of the ultrasound subsystem 124 (when present), the ablation subsystem 125, and the force sensing subsystem 126 can send signals to, and receive signals from, the processor 127. The processor 127 can be any type of processor for executing computer functions. For example, the processor 127 can execute program instructions stored within the memory 128 to carry out any function referenced herein, such as determine the magnitude and direction of a force experienced by the catheter 110.

The control unit 120 further includes an input/output subsystem 129 which can support user input and output functionality. For example, the input/output subsystem 129 may support the display 121 to display any information referenced herein, such as a graphic representation of tissue, the catheter 110, and a magnitude and direction of the force experienced by the catheter 110, amongst other options. Input/output subsystem 129 can log key and/or other input entries via the user input 122 and route the entries to other circuitry.

A single processor 127, or multiple processors, can perform the functions of one or more subsystems, and as such the subsystems may share control circuitry. Although different subsystems are presented herein, circuitry may be divided between a greater or lesser numbers of subsystems, which may be housed separately or together. In various embodiments, circuitry is not distributed between subsystems, but rather is provided as a unified computing system. Whether distributed or unified, the components can be electrically connected to coordinate and share resources to carry out functions.

Figure 3:
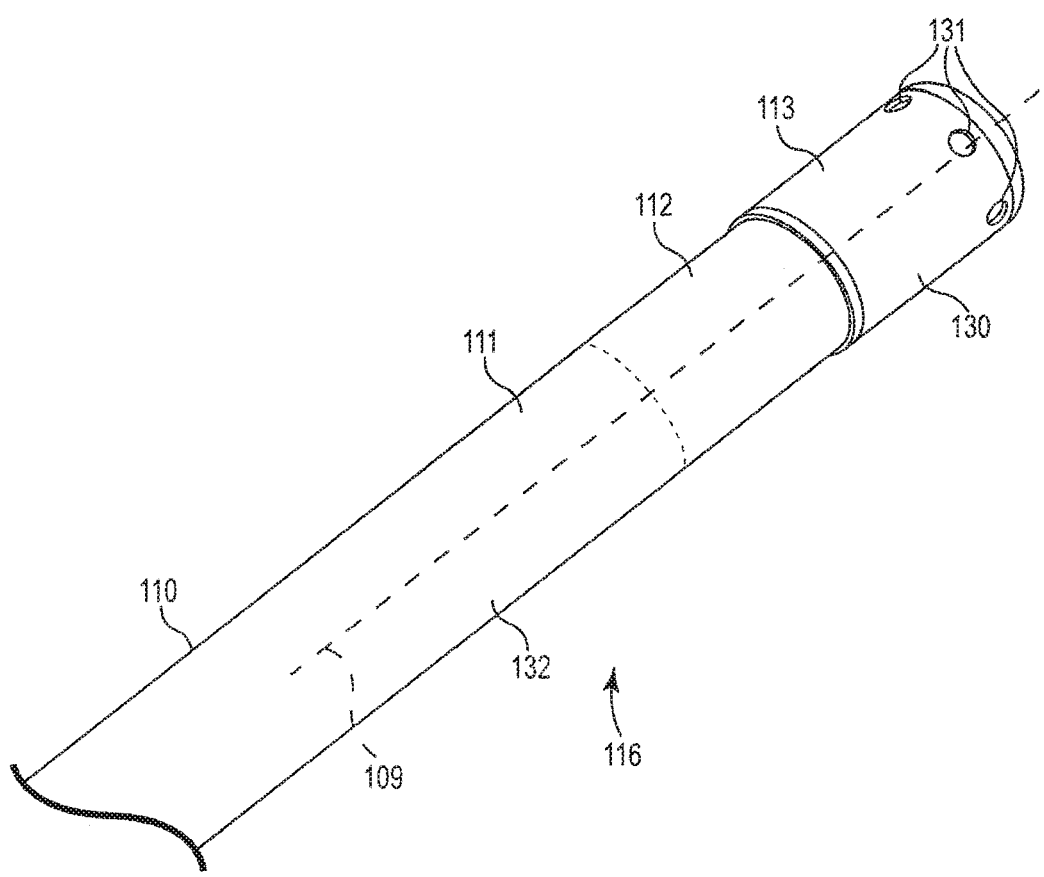
FIG. 3 shows a perspective view of a distal end of a catheter in accordance with various embodiments of this disclosure.

FIG. 3 illustrates a detailed view of the distal end 116 of the catheter 110. FIG. 3 shows a catheter shaft 132. The catheter shaft 132 can extend from the distal segment 113 to the handle 114 (FIG. 1A), and thus can define an exterior surface of the catheter 110 along the spring segment 112, the proximal segment 111, and further proximally to the proximal end 115 (FIG. 1A). The catheter shaft 132 can be a tube formed from various polymers, such as polyurethane, polyamide, polyether block amide, silicone, and/or other materials. In some embodiments, the catheter shaft 132 may be relatively flexible, and at least along the spring segment 112 may not provide any material mechanical support to the distal segment 113 (e.g., facilitated by thinning of the wall of the catheter shaft 132 along the spring segment 112).

As shown, the proximal segment 111 can be proximal and adjacent to the spring segment 112. The length of the proximal segment 111 can vary between different embodiments, and can be five millimeters to five centimeters, although different lengths are also possible. The length of the spring segment 112 can also vary between different embodiments and is dependent on the length of underlying features as will be further discussed herein. The spring segment 112 is adjacent to the distal segment 113. As shown in FIG. 3, the distal segment 113 can be defined by an electrode 130. The electrode 130 can be an ablation electrode. In some other embodiments, the distal segment 113 may not be an electrode. The electrode 130 can be in a shell form which can contain other components. The electrode 130 can include a plurality of ports 131. In some embodiments, the ports 131 may be fluidly connected to a source of irrigation fluid for flushing the volume adjacent to the distal segment 113. In some embodiments, one or more ultrasonic transducers, housed within the electrode 130, can transmit and receive signals through the ports 131 or through additional dedicated holes in the tip shell. Additionally or in place of the transducers, one or more miniature electrodes may be incorporated into the tip shell assembly.

Figure 4:
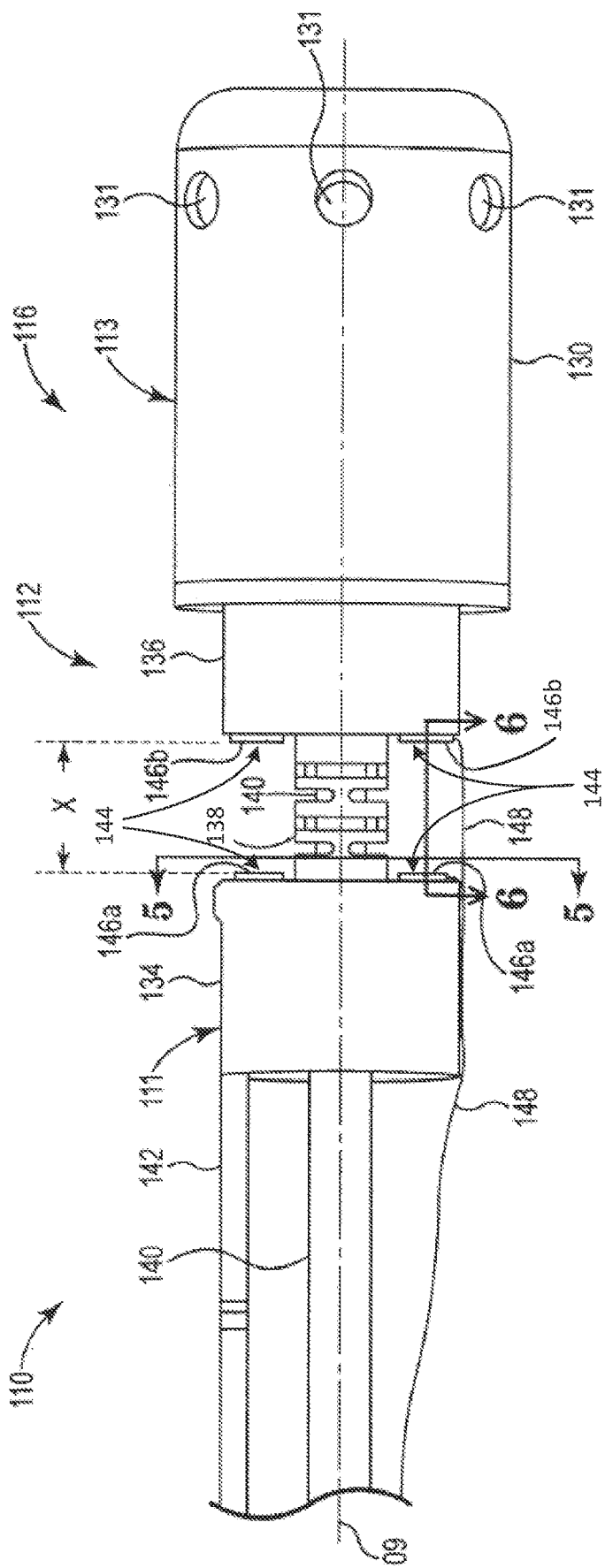
FIG. 4 shows a side view of the inside of the catheter shown in FIG. 3 in accordance with various embodiments of this disclosure.

FIG. 4 shows a side view of the inside of the distal end 116 of the catheter 110 of FIG. 3 after the removal of the catheter shaft 132 to expose various components that underlie the catheter shaft 132. As shown in FIG. 4, the proximal segment 111 may include a proximal hub 134, the distal segment 113 may include a distal hub 136, and the spring segment 112 may include an elastic element 138. In some embodiments, the proximal hub 134 and the distal hub 136 can be ring-like structures to which opposite ends of the elastic element 138 are attached to connect the proximal segment 111 to the distal segment 113. In other embodiments, the proximal hub 134, the distal hub 136, and the elastic element 138 may be integrally formed. One or both of the proximal hub 134 and the distal hub 136 can be formed from polymer materials, such as polyethylene, or PEEK, or can be formed from a metal, such as stainless steel. One or both of the proximal hub 134 and the distal hub 136 can be formed from a composite of metal, polymer, and/or other materials. The elastic element 138 provides predictable resistance to movement of the distal segment 113 relative to the proximal segment 111 according to a relationship governed by Hooke's law, in which force is a function of displacement and a spring constant. The elastic element 138 can be formed from a resilient material, for example, polymer materials, metals (e.g. stainless steel, nitinol), or other materials. In some embodiments, the elastic element 138 may be formed from a stainless steel hypotube.

The spring segment 112 can be a relatively flexible portion that is mostly or entirely mechanically supported by the elastic element 138. As such, the proximal hub 134 and the distal hub 136 can be stiffer than the elastic element 138 such that a force directed on the distal segment 113 causes the distal end 116 to bend along the elastic element 138 rather than along the distal segment 113 or the proximal segment 111.

In the base orientation, the proximal hub 134, the distal hub 136, and the elastic element 138 can be coaxially aligned with respect to the longitudinal axis 109, as shown in FIG. 4. For example, the longitudinal axis 109 can extend through the respective radial centers of each of the proximal hub 134, the distal hub 136, and the elastic element 138. An inner tube 140, described below in reference to FIG. 5, can extend through the catheter 110 (e.g., from the handle 114, FIG. 1A), through the proximal hub 134, the elastic element 138, and the distal hub 136.

A tether 142 can attach to a proximal end of the proximal hub 134. Considering FIGS. 1A and 4, together, the tether 142 can attach to a deflection mechanism within the handle 114 to cause deflection of the distal end 116. A knob, slider, or plunger on a handle 114 may be used to create tension or slack in the tether 142.

As shown in FIG. 4, the distal end 116 of the catheter 110 further includes at least one inductive sensor 144. The at least one inductive sensor 144 includes a first portion 146a disposed on an axially-facing distal surface of the proximal hub 134 and a second portion 146b disposed on an axially-facing proximal surface of the distal hub 136, as described in detail below in reference to FIG. 6. The first portion 146a and the second portion 146b are aligned opposite each other such that the two portions of the inductive sensor 144 are separated by a distance X. In some embodiments, such as the embodiment shown in FIG. 4, the at least one inductive sensor 144 includes a plurality of inductive sensors 144. Specifically, in the embodiment shown in FIG. 4, the plurality of inductive sensors 144 consists of three inductive sensors 144 (two visible in the side view of FIG. 4). The first portion 146a and the second portion 146b can be electrically connected by a flexible printed circuit 148. The flexible printed circuit 148 can also electrically connect the inductive sensors 144 to the catheter interface 123 (FIG. 2).

In operation, when a contact force on the distal segment 113 causes the distal end 116 to bend along the elastic element 138, the distance X between the first portion 146a and the second portion 146b of at least one of the inductive sensors 144 may change to varying degrees, depending on the location of the inductive sensor 144 relative to the contact force. Each of the inductive sensors 144 outputs a signal indicative of the displacement between the first portion 146a and the second portion 146b of the inductive sensor 144, as described below.

Figure 5:
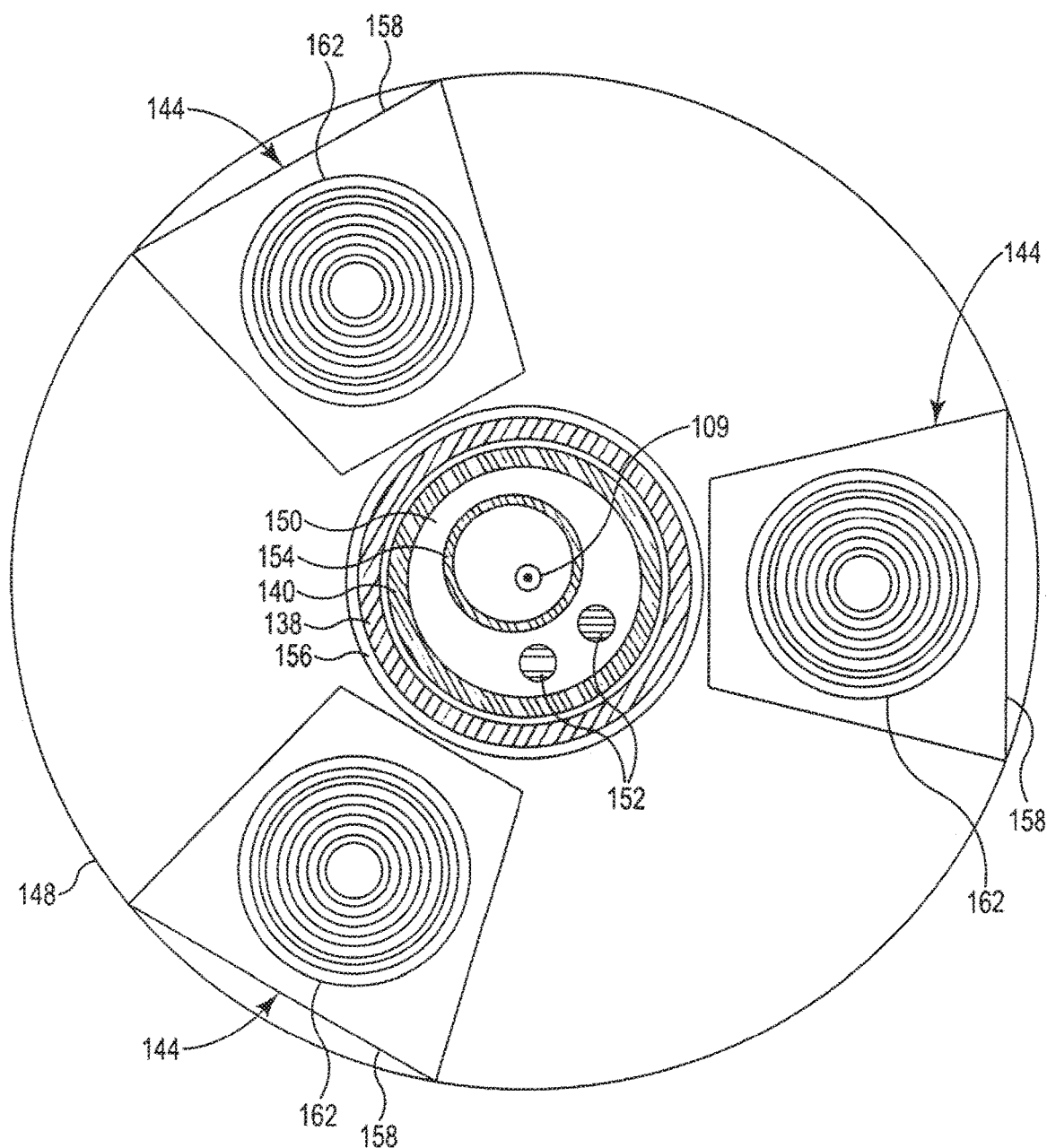
FIG. 5 shows a cross-sectional view of the catheter shown in FIG. 4 in accordance with various embodiments of this disclosure.

FIG. 5 shows a cross-sectional view of the distal end 116 of the catheter 110 shown in FIG. 4. As shown in FIG. 5, the inner tube 140 can include a lumen 150 within which one or more conductors 152 can extend from the proximal end 115 (FIG. 1A) to the distal segment 113, such as for connecting with one or more electrical elements (e.g., ultrasound transducer, electrode, or other component). Coolant fluid can additionally or alternatively be routed through the inner tube 140 by way of a coolant tube 154. In various embodiments, the catheter 110 is open irrigated (e.g., through the plurality of ports 131) to allow the coolant fluid to flow out of the distal segment 113. Various other embodiments concern a non-irrigated catheter 110. The flexible printed circuit 148 can be a physical substrate for the inductive sensors 144, in addition to electrically connecting them to the catheter interface 123 (FIG. 2). The flexible printed circuit 148 can include an opening 156 to accommodate the inner tube 140.

In the embodiment shown in FIG. 5, the distal end 116 of the catheter 110 includes three inductive sensors 144 at evenly spaced azimuth angles about the longitudinal axis 109 (circumferentially arrayed evenly about the longitudinal axis 109) and at the same radial distance from the longitudinal axis 109. In other embodiments, the inductive sensors 144 may not be at evenly spaced azimuth angles and/or at the same radial distance from the longitudinal axis 109. In the embodiment shown in FIGS. 4 and 5, the inductive sensors 144 are in a coplanar configuration. In other embodiments, the inductive sensors 144 may not be in a coplanar configuration.

Figure 6:
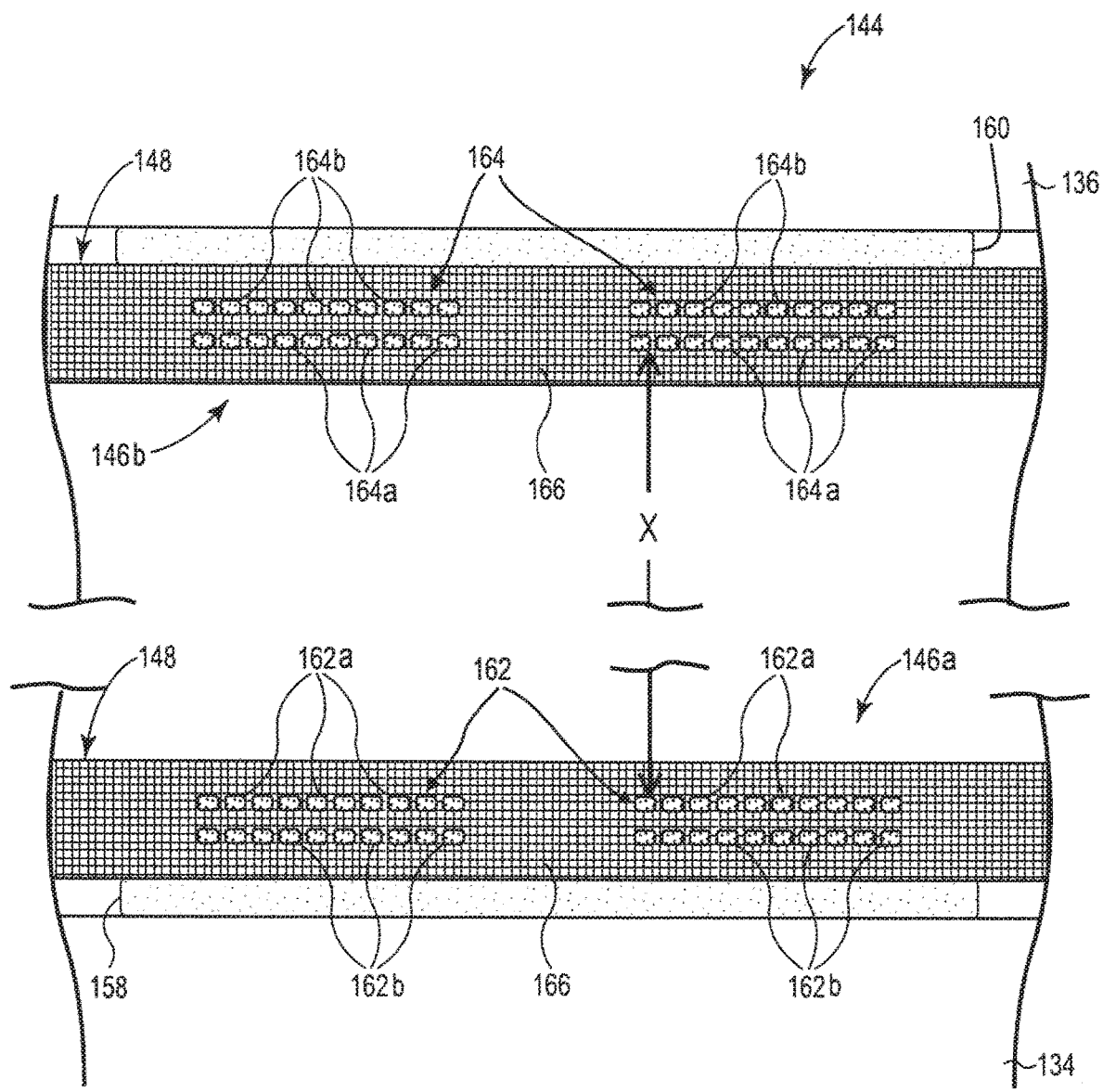
FIG. 6 shows a cross-sectional view of an inductive sensor in accordance with various embodiments of this disclosure.

FIG. 6 shows a cross-sectional view of one of the inductive sensors 144. Considering FIGS. 5 and 6 together, each of the inductive sensors 144 can include a first plate 158, a second plate 160, at least one first coil 162, and at least one second coil 164. The first portion 146a includes the first plate 158 and the at least one first coil 162. The second portion 146b includes the second plate 160 and the at least one second coil 164. The at least one second coil 164 is electrically connected in series with the at least one first coil 162. In some embodiments, the electrical connection between the at least one first coil 162 and the least one second coil 164 may be by way of the flexible printed circuit 148.

In the embodiment shown in FIG. 6, the at least one first coil 162 includes a plurality of axially-spaced coils 162a-162b, and the at least one second coil 164 includes a plurality of axially-spaced coils 164a-164b. The plurality of coils 162a-162b can be electrically connected in series and are axially spaced and aligned to form a stack of coils. Similarly, the plurality of coils 164a-164b can be electrically connected in series and form another stack of coils, as shown in FIG. 6. Other embodiments may include more than two axially spaced coils in each stack of coils. The coils 162a-162b and 164a-164b can be flat coils of a conductor, such as copper, gold, or combinations thereof, formed by concentric or spiral turns of conductive layers of the flexible printed circuit 148. In some embodiments, a thickness of each of the coils 162a-162b and 164a-164b can range from about 4 to about 10 microns and a width of individual turns can range from about 5 to about 10 microns. In other embodiments, the coils 162a-162b and 164a-164b can be physically separated from, but electrically connected to, the flexible printed circuit 148. Although the at least one first coil 162 and the at least one second coil 164 in the illustrated embodiment are identically sized coil stacks of coils 162a-162b and coils 164a-164b, it is understood that in other embodiments, the number of coils in each stack may not be the same.

The first plate 158 and the second plate 160 can be plates, films, sheets, or coatings of a high magnetic permeability material, for example, cobalt-based magnetic alloys, nickel-iron-based magnetic alloys, or purified iron. In some embodiments, the first plate 158 and the second plate 160 may each have a thickness ranging from about 10 microns to about 100 microns. In some embodiments, the 158 and the second plate 160 each have a relative permeability of at least about 1000, about 2000, about 10,000, about 20,000, about 50,000, or about 100,000, or at least about any value between any of the preceding values.

As shown in FIG. 6, the first plate 158 can be disposed on the proximal hub 134 and the second plate 160 can be disposed on the distal hub 136. The at least one first coil 162 can be disposed adjacent to the first plate 158 between the first plate 158 and the second plate 160. The at least one second coil 164 can be disposed adjacent to the second plate 160 between the first plate 158 and the second plate 160. The at least one first coil 162 and the at least one second coil 164 are aligned opposite each other such that the at least one first coil 162 and the at least one second coil 164 are separated by the distance X. The at least one first coil 162 can be insulated from the adjacent first plate 158 by an insulating material 166. In embodiments having a plurality of plurality of axially-spaced coils 162a-162b, the insulating material 166 can also insulate the coils 162a-162b from each other, except for a via (not shown) through the insulating material 166 to connect the coils 162a-162b in series. Similarly, the insulating material 166 can also insulate the at least one second coil 164 from the adjacent second plate 160 and, in some embodiments, insulate coils 164a-164b from each other except for a via (not shown) through the insulating material 166 to connect the coils 164a-164b in series.

In some embodiments, the coils 162a-162b and 164a-164b can be imbedded in the insulating material 166 as conductive layers of the flexible circuit 148, as shown in FIG. 6. In some embodiments, the thickness of the insulating material 166 between the each of the coils 162a-162b and between the coils 162a-162b and the first plate 158 can be between about 6 microns and about 30 microns. In some embodiments, the thickness of the insulating material 166 between each of the coils 164a-164b and between the coils 164a-164b and the second plate 160 can be between about 6 microns and about 30 microns. The insulating material 166 can be, for example, a flexible, insulating polymer, such as a polyimide.

In some embodiments, edges of the first plate 158 and the second plate 160 can extend beyond edges of the at least one first coil 162 and the at least one second coil 164, as shown in FIGS. 5 and 6, to contain and direct fields produced by the at least one first coil 162 and the at least on second coil 164. Although the first plate 158 and the second plate 160 are illustrated as relatively thin and flat, it is understood that embodiments may include plates that are not relatively thin and/or not relatively flat.

In operation, the force sensing subsystem 126 (FIG. 2) supplies to each of the inductive sensors, an alternating sinusoidal excitation current of frequency f and magnitude M to the at least one first coil 162 and the at least one second coil 164, which are electrically connected in series. The time-dependent excitation current M(t) may be described according to Equation 1:

$$M(t) = M \sin(2\pi ft).$$ Eq. 1

The excitation current M(t) produces an alternating magnetic field of magnetic flux through and around the first coil 162 and the second coil 164. The excitation current M(t) passing through the first coil 162 and the second coil 164 develops a time dependent voltage having an amplitude V(t) across the first coil 162 and the second coil 164. The voltage V(t) is a function of the magnitude of the time derivative of the excitation current M(t) and the inductance L of each of the first coil 162 and the second coil 164. The voltage V(t) may be described according to Equation 2:

$$V(t) = L 2\pi f M \cos(2\pi ft).$$ Eq. 2

The inductance L of each of the first coil 162 and the second coil 164 can be a function of a number of coil turns N, a cross-sectional coil area A, a coil length G, and the effective magnetic permeability $\mu(X)$ proximate to the first coil 162 and the second coil 164. The inductance L may be described according to Equation 3:

$$L = N^2 A \mu(X)/G.$$ Eq. 3

The cross-sectional area A is a fixed parameter. However, an "effective" length G and an "effective" number of turns N may change as the distance X between the first coil 162 and the second coil 164 changes. For example, when the first portion 146a of the inductive sensor 144 is not displaced relative to the second portion 146b by a contact force on the distal segment 113, the distance X between the first coil 162 and the second coil 164 can be large enough that the first coil 162 and the second coil 164 behave as two separate coils electrically connected in series, with little magnetic flux interaction between the first coil 162 and the second coil 164. Under such conditions, the inductance L of the inductive sensor 144 may be about twice that of the inductance of either of the first coil 162 or the second coil 164 having N turns and a length G. When the first portion 146a of the inductive sensor 144 is displaced relative to the second portion 146b by a contact force on the distal segment 113, the distance X is smaller and the magnetic flux generated by the first coil 162 begins to interact with the second coil 164, and vice versa. With the increased magnetic flux interaction, the first coil 162 and the second coil 164 behave as a single, longer coil with an effective length greater than 2G and having 2N turns. This effect results in a net increase in inductance due to the squared nature of the turns (N) parameter compared with the first order nature of the length parameter (G). At larger displacements, the effective length may be close to 2G and the inductance L may be as much as four times that of the inductance of the first coil 162 or the second coil 164 alone. Thus, this effect alone may as much as double the inductance L at larger displacements.

The effective magnetic permeability $\mu(X)$ also contributes to an increase in inductance when the inductive sensor 144 is displaced by a contact force on the distal segment 113. The effective magnetic permeability $\mu(X)$ is a function of the distance X between the first coil 162 and the second coil 164. At greater displacements and smaller distances X, the overall volume of the first coil 162 and the second coil 164 is smaller and thus, a greater fraction of the volume is occupied by the high permeability material of the first plate 158 and the second plate 160. The increased volume fraction occupied by the high permeability material results in an increased effective magnetic permeability $\mu(X)$. The increased effective permeability $\mu(X)$ increases the inductance L of the first coil 162 and the second coil 164 as describe in Equation 3 above.

Considering Equations 2 and 3 together along with the above discussion, each of the inductive sensors 144 can output a change in the voltage amplitude V(t) resulting from a change in the distance X between the first coil 162 and the second coil 164. The voltage amplitude V(t) will increase as the distance X between the first coil 162 and the second coil 164 decreases due to the increase in the degree of magnetic flux interaction between the first coil 162 and the second coil 164 and to the increase in the effective magnetic permeability in the environment around the first coil 162 and the second coil 164.

In some embodiments, the alternating magnetic field of magnetic flux is almost entirely contained within and between the first plate 158 and the second plate 160 because of their high magnetic permeability and because they extend beyond the edges of the first coil 162 and the second coil 164 to effectively magnetically encapsulate the first coil 162 and the second coil 164. By containing the alternating magnetic field of magnetic flux, the inductive sensors 144 are also less likely to generate external magnetic fields which could interfere with other systems, such as, for example, magnetic sensors used for navigation, as described below.

As shown in FIG. 5, the three inductive sensors 144 are at evenly spaced azimuth angles about the longitudinal axis 109 (circumferentially arrayed evenly about the longitudinal axis 109) and at the same radial distance from the longitudinal axis 109. If the force exerted on the distal segment 113 of the catheter 110 is coaxial with the longitudinal axis 109, then each of the inductive sensors 144 will output equal amounts of a change in the amplitude of the alternating voltage V(t) indicating an equal change in the distance X between the at least one first coil 162 and the at least one second coil 164 for each of the inductive sensors 144. Based on these equal changes, the control circuitry can calculate a magnitude of the force exerted on the distal segment 113 based on the change in the distance X between the at least one first coil 162 and the at least one second coil 164 for each of the inductive sensors 144, and the spring constant of the elastic element 138, according to Hooke's law. The control circuitry can also determine that the force is coaxial with the longitudinal axis 109 because the change in the amplitude of the alternating voltage V(t) is the same for each of the three inductive sensors 146.

If the force is not coaxial with the longitudinal axis 109, then distal segment 113 will tend to curl or shift radially away from the force with respect to the proximal segment 111. In such cases, the change in the amplitude of the alternating voltage V(t) for each of the inductive sensors 144 will not be equal. For example, in some cases, each of the inductive sensors 144 may output a different change in the amplitude of the alternating voltage V(t). In other cases, one or more inductive sensors 144 may output a different change in the amplitude of the alternating voltage V(t) compared to one or more other inductive sensors 144. Generally, the one or more inductive sensors 144 indicating the largest change in the amplitude of the alternating voltage V(t) indicate the opposite direction from which the force is coming. Based on this, the magnitude and the direction (e.g., unit vector) of the force can be determined by the control circuitry.

Once assembled, the catheter 110 may undergo a calibration step, either at a factory or just before use by a physician. In such a step, a plurality of forces of known magnitude and direction can be placed, in sequence, on the distal segment 113 to displace the distal segment 113 relative to the proximal segment 111, while the inductive sensors 144 output changes in the amplitude of their corresponding alternating voltage V(t). A mathematical relationship can be generated based on the linearity of Hooke's law, wherein a limited number of calibration steps are performed to determine the change in the amplitude of the alternating voltage V(t), and interpolation and/or extrapolation can be computed based on these calibration values. For example, the spring constant can be determined for the elastic element 138 such that subsequent changes in the distance X between the at least one first coil 162 and the at least one second coil 164 can be multiplied by the spring constant to determine the magnitude of the force acting on the distal segment 113. The changes in the distance X for multiple inductive sensors 144 can be factored for determining an overall magnitude and direction for the force.

The magnitude can be represented in grams or another measure of force. The magnitude can be presented as a running line graph, bar graph or graphic symbol varying with color or intensity that moves over time to show new and recent force values. The direction can be represented as a unit vector in a three dimensional reference frame (e.g., relative to an X, Y, and Z axes coordinate system). In some embodiments, a three dimensional mapping function can be used to track the three dimensional position of the distal end 116 of the catheter 110 in the three dimensional reference frame. Magnetic fields can be created outside of the patient and sensed by a sensor (not shown) that is sensitive to magnetic fields within distal end 116 of the catheter 110 to determine the three dimensional position and special orientation of the distal end 116 of the catheter 110 in the three dimensional reference frame. The direction can be represented relative to the distal end 116 of the catheter 110. For example, a line projecting to, or from, the distal segment 113 can represent the direction of the force relative to the distal segment 113. Similarly, a graphic symbol with varying color and/or intensity and/or shape could be utilized to represent the magnitude and/or the direction of the force. Such representations can be made on a display as discussed herein.

The magnitude and direction of the force can be used for navigation by providing an indicator when the catheter encounters tissue and/or for assessing the lesioning of tissue by determining the degree of contact between the lesioning element and the tissue, among other options. In some embodiments, a force under 10 grams is suboptimal for lesioning tissue (e.g., by being too small) while a force over 40 grams is likewise suboptimal for lesioning tissue (e.g., by being too large). Therefore, a window between 10 and 40 grams may be ideal for lesioning tissue and the output of the force during lesioning may provide feedback to the user to allow the user to stay within this window. Of course, other force ranges that are ideal for lesioning may be used.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A catheter adapted to measure a contact force, the catheter comprising:
   a proximal segment;
   a distal segment;
   a spring segment extending from the proximal segment to the distal segment, the spring segment configured to permit displacement between the distal segment and the proximal segment in response to an application of the contact force on the distal segment, the proximal segment includes a proximal hub, the distal segment includes a distal hub, the spring segment includes an elastic element, and each of the proximal hub and the distal hub are structures to which opposite ends of the elastic element are attached to connect the proximal segment to the distal segment; and a plurality of inductive sensors, wherein each inductive sensor of the plurality of inductive sensors includes:
a first plate having a relative permeability of at least 1000 disposed on the proximal segment;
a second plate having a relative permeability of at least 1000 disposed on the distal segment opposite the first plate;
at least one first coil disposed adjacent to the first plate between the first plate and the second plate; and
at least one second coil disposed adjacent to the second plate opposite the first coil between the first plate and the second plate, the at least one second coil electrically connected in series with the at least one first coil, wherein the at least one first coil and the at least one second coil are configured to output a signal indicative of a change in a distance between the at least one first coil and the at least one second coil,
wherein the plurality of inductive sensors comprises at least a first inductive sensor, a second inductive sensor, and a third inductive sensor circumferentially arrayed about a longitudinal axis of the catheter, wherein the first and second plates are exterior to the elastic element and aligned so as to face opposite to each other, wherein the distal segment is configured to bend along the spring segment such that a value representing the change in the distance between the at least one first coil and the at least one second coil of the first inductive sensor of the plurality of inductive sensors is configured to be different from a value of the change in the distance between the at least one first coil and the at least one second coil of the second inductive sensor of the plurality of inductive sensors.

2. The catheter of claim 1, wherein edges of the first plate extend beyond edges of the at least one first coil and edges of the second plate extend beyond edges of the at least one second coil.

3. The catheter of claim 1, wherein the at least one first coil is a flat coil of one or more flexible printed circuit conductive layers and the at least one second coil is a flat coil of one or more flexible printed circuit conductive layers.

4. The catheter of claim 1, wherein the distal segment includes an ablation element configured to deliver ablation therapy.

5. The catheter of claim 1, wherein the first plate and the second plate each have a relative permeability greater than 2000.

6. The catheter of claim 1, wherein the spring segment includes the elastic element connecting the proximal segment to the distal segment to permit the displacement between the distal segment and the proximal segment in response to an application of the contact force on the distal segment and to resiliently reverse the displacement upon removal of the contact force from the distal segment.

7. The catheter of claim 1, wherein the signal indicative of the change in the distance between the at least one first coil and the at least one second coil is based on a change in an alternating voltage amplitude resulting a least in part from changes in a degree of magnetic flux interaction between the at least one first coil and the at least one second coil caused by changes in a distance between the at least one first coil and the at least one second coil.

8. A system adapted to measure a catheter contact force, the system comprising:

a catheter including:
a proximal segment;
a distal segment;
a spring segment extending from the proximal segment to the distal segment, the spring segment configured to permit displacement between the distal segment and the proximal segment in response to an application of the catheter contact force on the distal segment, the proximal segment including a proximal hub, the distal segment including a distal hub, the spring segment including a flexible portion and an elastic element that mechanically supports the flexible portion, each of the proximal hub and the distal hub are structures to which opposite ends of the elastic element are attached to connect the proximal segment to the distal segment; and
a plurality of inductive sensors, wherein each inductive sensor of the plurality of inductive sensors includes:
a first plate having a relative permeability of at least 1000 disposed on the proximal segment;
a second plate having a relative permeability of at least 1000 disposed on the distal segment opposite the first plate;
at least one first coil disposed adjacent to the first plate between the first plate and the second plate; and
at least one second coil disposed adjacent to the second plate between the first plate and the second plate opposite the first coil, the at least one second coil electrically connected in series with the at least one first coil, wherein the at least one first coil and the at least one second coil are configured to output a signal indicative of a change in a distance between the at least one first coil and the at least one second coil; and
control circuitry configured to receive, for each of the plurality of inductive sensors, the signal indicative of the change in the distance between the at least one first coil and the at least one second coil, and calculate at least one of a magnitude and a direction of the catheter contact force based at least in part on the received signal indicative of the change in the distance between the at least one first coil and the at least one second coil,
wherein the plurality of inductive sensors comprises at least a first inductive sensor, a second inductive sensor, and a third inductive sensor circumferentially arrayed about a longitudinal axis of the catheter, wherein the first and second plates are exterior to the elastic element and aligned so as to face opposite to each other, wherein the distal segment is configured to bend along the spring segment such that a value representing the change in the distance between the at least one first coil and the at least one second coil of a first inductive sensor of the plurality of inductive sensors is configured to be different from a value of the distance between the at least one first coil and the at least one second coil of a second inductive sensor of the plurality of inductive sensors.

9. The system of claim 8, wherein the spring segment includes the elastic element connecting the proximal segment to the distal segment to permit the displacement between the distal segment and the proximal segment in response to an application of the catheter contact force on the distal segment, wherein the control circuitry is further configured to calculate the at least one of the magnitude and the direction of the catheter contact force based at least in part on a spring constant for the elastic element.

10. The system of claim 8, wherein the control circuitry is further configured to deliver an alternating sinusoidal electrical current to the at least one first coil and the at least one second coil of each of the plurality of inductive sensors to produce an alternating voltage across the at least one first coil and the at least one second coil of each of the plurality of inductive sensors.

11. The system of claim 8, further comprising a display, wherein the control circuitry is configured to graphically indicate on the display the magnitude and the direction of the catheter contact force.

12. The system of claim 8, wherein edges of the first plate extend beyond edges of the at least one first coil and edges of the second plate extend beyond edges of the at least one second coil.

13. The system of claim 8, wherein the at least one first coil is a flat coil of one or more flexible printed circuit conductive layers and the at least one second coil is a flat coil of one or more flexible printed circuit conductive layers.

14. The system of claim 8, wherein the distal segment includes an ablation element configured to deliver ablation therapy.

15. The system of claim 8, wherein the output signal indicative of the change in the distance between the at least one first coil and the at least one second coil is based on a change in an alternating voltage amplitude resulting from changes in a degree of magnetic flux interaction between the at least one first coil and the at least one second coil caused by changes in a distance between the at least one first coil and the at least one second coil.

* * * * *